(12) United States Patent
Sun et al.

(10) Patent No.: US 12,239,703 B2
(45) Date of Patent: Mar. 4, 2025

(54) COMPOSITE-TYPE NANO-VACCINE PARTICLE

(71) Applicant: NEUCOLOGY BIOMEDICAL INC., Richmond (CA)

(72) Inventors: Chung Chin Sun, Richmond (CA); Dean Mo Liu, Surrey (CA)

(73) Assignee: Nuecology Biomedical Inc., Richmond (CA)

( * ) Notice: Subject to any disclaimer, the term of this patent is extended or adjusted under 35 U.S.C. 154(b) by 371 days.

(21) Appl. No.: 17/662,969

(22) Filed: May 11, 2022

(65) Prior Publication Data

US 2022/0378905 A1 Dec. 1, 2022

Related U.S. Application Data

(60) Provisional application No. 63/193,253, filed on May 26, 2021.

(51) Int. Cl.
*A61K 39/215* (2006.01)
*A61K 39/00* (2006.01)

(52) U.S. Cl.
CPC ........ *A61K 39/215* (2013.01); *A61K 2039/55505* (2013.01); *A61K 2039/55561* (2013.01); *A61K 2039/6087* (2013.01)

(58) Field of Classification Search
CPC ........ A61K 39/215; A61K 2039/55505; A61K 2039/55561; A61K 2039/6087
See application file for complete search history.

(56) References Cited

U.S. PATENT DOCUMENTS

| | | | |
|---|---|---|---|
| 6,406,705 B1 * | 6/2002 | Davis | A61K 39/12 424/282.1 |
| 7,285,289 B2 | 10/2007 | Nagy et al. | |
| 8,802,076 B2 | 8/2014 | Abraham et al. | |
| 9,439,859 B2 * | 9/2016 | Alexis | A61P 37/04 |
| 9,539,210 B2 | 1/2017 | Von Andrian et al. | |

(Continued)

FOREIGN PATENT DOCUMENTS

| | | |
|---|---|---|
| WO | 2012156564 A2 | 11/2012 |
| WO | 2015116568 A3 | 8/2015 |

(Continued)

OTHER PUBLICATIONS

Foged, C. et al. Particle size and surface charge affect particle uptake by human dendritic cells in an in vitro model. 2005. International Journal of Pharmaceutics. 298, 2(25), 315-322. (Year: 2005).*

(Continued)

*Primary Examiner* — Jennifer A Berrios
*Assistant Examiner* — Chasity P Janosko
(74) *Attorney, Agent, or Firm* — Rosenberg, Klein & Lee

(57) ABSTRACT

The present invention discloses a composite-type nano-vaccine particle, which comprises an active ingredient selected from spike RBD protein of COVID-19, two adjuvants as aluminium salt nanoparticle and synthetic oligo-nucleotides, and an amphiphilic alginate-based nanocarrier encapsulating the active ingredient and the two adjuvants. The composite-type nano-vaccine particle has a particle size ranging from 300 nm to 1400 nm in diameter.

10 Claims, 15 Drawing Sheets
(2 of 15 Drawing Sheet(s) Filed in Color)
Specification includes a Sequence Listing.

(56) References Cited

U.S. PATENT DOCUMENTS

| | | |
|---|---|---|
| 2008/0044484 A1 | 2/2008 | Minev |
| 2008/0124350 A1 | 5/2008 | Mumper et al. |
| 2023/0302116 A1* | 9/2023 | Hecht .................... A61K 39/12 |

FOREIGN PATENT DOCUMENTS

| | | | |
|---|---|---|---|
| WO | 2015130584 A2 | 9/2015 | |
| WO | 2016081783 A1 | 5/2016 | |
| WO | 2016109792 A8 | 7/2016 | |
| WO | WO-2018136012 A1 * | 7/2018 | ............ A61K 31/047 |
| WO | WO-2021174365 A1 * | 9/2021 | ............. A61K 31/12 |
| WO | WO-2022043551 A2 * | 3/2022 | ............. A61K 39/12 |

OTHER PUBLICATIONS

Donaldson B et al., Virus-like particle vaccines: immunology and formulation for clinical translation, Expert Review of Vaccines. 2018; 17(9): 833-849).

Blakney, A. K. et al., Big is Beautiful: Enhanced saRNA Delivery and Dmmunogenicity by a Higher Molecular Weight, Bioreducible, Cationic Polymer. ACS Nano14, 5711-5727 (2020).

Kim, E. et al., Microneedle array delivered recombinant coronavirus vaccines: Immunogenicity and rapid translational development, EBioMedicine 55, 102743 (2020).

Pardi, N. et al., Expression kinetics of nucleoside-modified mRNA delivered in lipid nanoparticles to mice by various routes, J. Control. Release 217, 345-351 (2015).

Geall, A. J. et al., Nonviral delivery of self-amplifying RNA vaccines. Proc. Natl Acad. Sci. USA 109, 14604-14609 (2012).

Paston et al., Cancer Vaccines, Adjuvants, and Delivery Systems, Front. Immunol., Mar. 30, 2021.

Chatzikleanthous et al., Lipid-Based Nanoparticles for Delivery of Vaccine Adjuvants and Antigens: Toward Multicomponent Vaccines, Mol. Pharmaceutics 2021, 18, 8, 2867-2888.

E. Samaridou et al., Lipid nanoparticles for nucleic acid delivery: Current perspectives, Advanced Drug Delivery Reviews, 154-155, 2020, 37-63.

Hou et al., Lipid nanoparticles for mRNA delivery, Nature Reviews Materials, 6, 1078-1094, 2021.

Evers et al., State-of-the-Art Design and Rapid-Mixing Production Techniques of Lipid Nanoparticles for Nucleic Acid Delivery, Small Methods, 2(4), 2018.

McKay et al., Self-amplifying RNA SARS-COV-2 lipid nanoparticle vaccine candidate induces high neutralizing antibody titers in mice, Nature Communications, 11, 3523, 2020.

Blakney, A. K., McKay, P. F., Yus, B. I., Aldon, Y. & Shattock, R. J., Inside out: optimization of lipid nanoparticle formulations for exterior complexation and in vivo delivery of saRNA. Gene Ther. 26, 363-372, 2019.

* cited by examiner

SEQUENCE LISTING

```
<160> NUMBER OF SEQ ID NOS: 2

<210> SEQ ID NO 1
<211> LENGTH: 224
<212> TYPE: PRT
<213> ORGANISM: SARS-CoV-2 (COVID-19)

<400> SEQUENCE: 1

Met Glu Lys Gly Ile Tyr Gln Thr Ser Asn Phe Arg Val Gln Pro Thr
1               5                   10                  15

Glu Ser Ile Val Arg Phe Pro Asn Ile Thr Asn Leu Cys Pro Phe Gly
            20                  25                  30

Glu Val Phe Asn Ala Thr Arg Phe Ala Ser Val Tyr Ala Trp Asn Arg
        35                  40                  45

Lys Arg Ile Ser Asn Cys Val Ala Asp Tyr Ser Val Leu Tyr Asn Ser
    50                  55                  60
```

```
Ala Ser Phe Ser Thr Phe Lys Cys Tyr Gly Val Ser Pro Thr Lys Leu
 65                  70                  75                  80

Asn Asp Leu Cys Phe Thr Asn Val Tyr Ala Asp Ser Phe Val Ile Arg
                 85                  90                  95

Gly Asp Glu Val Arg Gln Ile Ala Pro Gly Gln Thr Gly Lys Ile Ala
            100                 105                 110

Asp Tyr Asn Tyr Lys Leu Pro Asp Asp Phe Thr Gly Cys Val Ile Ala
        115                 120                 125

Trp Asn Ser Asn Asn Leu Asp Ser Lys Val Gly Gly Asn Tyr Asn Tyr
    130                 135                 140

Leu Tyr Arg Leu Phe Arg Lys Ser Asn Leu Lys Pro Phe Glu Arg Asp
145                 150                 155                 160

Ile Ser Thr Glu Ile Tyr Gln Ala Gly Ser Thr Pro Cys Asn Gly Val
                165                 170                 175

Glu Gly Phe Asn Cys Tyr Phe Pro Leu Gln Ser Tyr Gly Phe Gln Pro
            180                 185                 190

Thr Asn Gly Val Gly Tyr Gln Pro Tyr Arg Val Val Val Leu Ser Phe
        195                 200                 205

Glu Leu Glu Gly Lys Leu Gly Ile Arg Pro Gly Thr Glu Leu Ala Leu
    210                 215                 220

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotides (ODN) that contain
      such CpG motifs (CpG-ODNs) mimic microbial DNA.

<400> SEQUENCE: 2
tccatgacgt tcctgacgtt                                            20
```

COMPOSITE-TYPE NANO-VACCINE PARTICLE

This application claims priority of U.S. provisional patent application No. 63/193,253 filed on 26 May 2021, the entire contents of all of which are hereby incorporated by reference.

REFERENCE TO THE SEQUENCE LISTING

This application contains a Sequence Listing which has been submitted in ASCII format via EFS-Web/Patent Center and is hereby incorporated by reference in its entirety. Said ASCII file, modified on May 9, 2022, is named "1035-2892-SEQUENCE-LISTING-MAY09-2022.txt" and is 2,454 bytes in size.

BACKGROUND OF THE INVENTION

Field of the Invention

The present invention relates to preparing a virus-like particle as a pharmaceutical composition. More specifically, the virus-like particle is a composite-type vaccine-adjuvant containing nanoparticle applicable to medical treatment or vaccinology research.

Description of the Prior Art

Virus-like particle platform technology is a biotechnology that has flourished in the field of human virus vaccines in recent years. The purpose is to produce the structural protein of the pathogenic virus and then assemble it into particles to mimic the original three-dimensional structure of the virus (Donaldson B et al., 2018).

Encapsulating vaccine into a solid entity to form a nano-sized vaccine carrier has been received great attention over decades. This solid entity can be a polymer, liposome, protein, silica, carbon, metal or metal oxide. However, potency of the encapsulating vaccine may be altered considerably, dependent on the process of encapsulating procedure and the biological and chemical nature of the vaccine itself. Besides, vaccine is frequently accompanied with the aid of an adjuvant, in order to boost immunological response after vaccination, to enhance the immunological potency of the vaccine. Therefore, co-encapsulating the vaccine of interest as a first active ingredient with improved stabilization and adjuvant as a second active ingredient, and deliver simultaneously on the site of administration can be a synergistic design.

LNPs are lipid-based drug delivery systems that carry nucleic acid material. These systems primarily rely on four lipid components: a PEG lipid, amino (cationic) lipid, structural lipid, and cholesterol. The cationic lipids are used to sequester the genetic material through a charge-charge interaction. Currently available vaccine nanocarriers, such as LNP-based mRNA vaccines, virus-based vaccine carriers, show positively charged surface, and their design is based on surface charging which allows for a cellular intake. Yet, electrostatic interactions are between and among cations and anions, and electrostatic forces fall off gradually with distance ($1/r^2$, where r is the distance between the ions). Therefore, unless approaching close enough, where the electrostatic interaction can be evolved efficiently, renders inefficient cellular intake of the LNP carriers.

Currently, the leading mRNA COVID-19 vaccines are all utilizing LNP technology. Together with the mRNA, these components form particles of about 60-100 nm in size by using a rapid mixing production technique (Evers et al., 2018). The SARS-CoV-2 vaccine candidates nCoVsaRNA and ARCoV, for example, have average particle sizes of 75 nm and 89 nm, respectively (McKay et al., 2020). Conventional lipid-based mRNA vaccine-carrying particles are small in size so that more injection doses (for instance, 30 and 100 micrograms of mRNA per dose of Pfizer/BNT and Moderna vaccine, respectively, where more chemical ingredients as recipients are dosed in the meantime) are required in order to reach therapeutically sufficient amount of mRNA vaccine to trigger immunological efficacy, however, the associated probability of side effects is also higher.

SUMMARY OF THE INVENTION

To enhance vaccine potency while reducing the injection doses and the probability of side effects, the present invention provides an AGO™ (amphiphilic polysaccharide) co-encapsulates vaccine, i.e., peptide-based vaccine or protein-based vaccine, and adjuvants included both aluminium salt nanoparticle and synthetic oligonucleotides.

The present invention is a composite-type nano-vaccine particle that has a particle size ranging from 300 nm to 1400 nm in diameter, which allows high amount of dual-adjuvant-antigen complex co-delivered into the targeting cells in host, permitting higher vaccine concentration to work out with desired immunological response in a lower dosing protocol, and in the meantime, no other chemical ingredients such as surfactants, interfacial agents, or colloidal stabilizers such as salts are required in the composite nano-vaccine protocol. Furthermore, the composite-type nano-vaccine particles of the present invention is proven highly efficient cellular endocytosis by demonstrating a strong donor-receptor binding. The design concept of this composite nano-vaccine is virtually different from what has been reported in the literature and used in current clinical protocols, which can be essentially considered as a nano-platform for a wide variety of vaccine-adjuvant combinations with immunological synergy.

A detailed description of further features in the present invention is given below so that a person skilled in the art is allowed to understand and carry out the technical contents of the present invention, and can readily comprehend the objectives and advantages of the present invention after reviewing the contents disclosed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings are included to provide a further understanding of the invention, and are incorporated in and constitute a part of this specification. The drawings illustrate embodiments of the invention and, together with the description, serve to explain the features and advantages of the invention. In the drawings.

DESCRIPTION OF THE PREFERRED EMBODIMENTS

Figure 1:
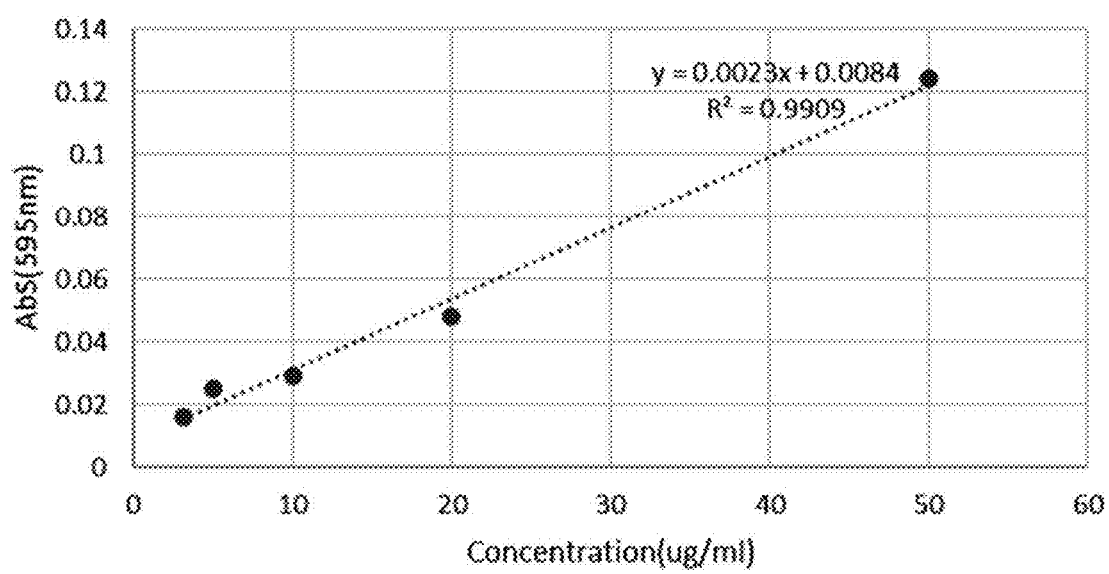
FIG. 1 is a calibration curve of spike RBD protein in Adsorption experiment according to an embodiment of the present invention.

Embodiments of the present invention disclose the preparation of a composite-type nano-vaccine particle, measurement of diameter and zeta potential of the nano-vaccine particle, demonstration of cellular endocytosis and in vitro cytotoxicity test.

I. Preparation of Composite-Type Nano-Vaccine Particle

Main Materials:

The present invention utilized an amphiphilic polysaccharide with controlled low-molecule weight termed as AGO™ (amphiphilic polysaccharide) purchased from Nuecology Biomedical Inc. British Columbia, Canada. The AGO™ (amphiphilic polysaccharide) functions as an amphiphilic alginate-based nanocarrier encapsulating vaccine as the active ingredient and adjuvants simultaneously. The AGO™ (amphiphilic polysaccharide) showed a self-assembly behavior in aqueous solution to form spherical nanoparticles, excellent structural stability, colloidal stability for a time period of months and biocompatibility in vitro and in vivo. The AGO™ (amphiphilic polysaccharide) can form an AGO™ (amphiphilic polysaccharide) nanoparticle in aqueous medium that can be used as a biomedical material for multifunctional applications, such as a delivery system for an active agent, including but not limited to a drug or a biological agent or material comprising a peptide, a protein, an antibody, a serum product, a vaccine, a plurality of cells or stem cells or a combination of multiple active agents of various physicochemical properties, such as a mixture of water-soluble or lipid-soluble ingredients, or a combination of organic and inorganic active agents.

Vaccine material as active ingredient comprises spike RBD protein. The amino acid sequence of the spike RBD protein is set forth by SEQ ID NO:1, as a model protein. pH-dependent charge of the spike RBD protein presents as the table below:

| pH | charge |
| --- | --- |
| 4.00 | 16.7 |
| 4.50 | 11.4 |
| 5.00 | 6.8 |
| 5.50 | 4.4 |
| 6.00 | 3.4 |
| 6.50 | 3.0 |
| 7.00 | 2.7 |
| 7.50 | 2.1 |
| 8.00 | 0.6 |
| 8.50 | −2.1 |
| 9.00 | −5.6 |
| 9.50 | −10.6 |
| 10.00 | −17.9 |

Because of the common mutation of SARS-CoV-2 (COVID-19), the amino acid sequence can be different, possibly only a few or few tens of amino acids. In order to perform a large amount of physical adsorption on the spike protein, so as to achieve the nano-vaccine effect, the present invention utilized change in charging in accordance with pH adjustment of the solution used in the preparation of a composite-type nano-vaccine particle. In the present invention, the AGO™ (amphiphilic polysaccharide) not merely encapsulates the spike RBD protein, but the AGO™ (amphiphilic polysaccharide) and the spike RBD protein may conjugate together.

Adjuvants comprise aluminium salt ($Al(OH)_3$) and a synthetic oligonucleotides (CpG-ODN). The aluminium salt has a particle size ranging between 5 nm to 30 nm, and it was used to adsorb physically with the spike RBD protein to form a core-shell nanoparticle, termed as a dual-adjuvant nanoparticle. The synthetic oligonucleotides (CpG-ODN) sequence is set forth by SEQ ID NO:2. The general information of CpG-ODN is as follows: unmethylated CG dinucleotides within particular sequence contexts are responsible for the immunostimulatory activity of bacterial DNA. Synthetic oligonucleotides (ODN) that contain such CpG motifs (CpG-ODNs) mimic microbial DNA. The innate immune system of vertebrates has the ability to recognize CpG motifs in microbial DNA via the Toll-like receptor (TLR) 9.

Adsorption Experiment:

Took 0.5 ml $Al(OH)_3$ solution (1 mg/ml) and 0.5 ml spike RBD protein solution (50 µg/ml) to form a mixture of 500 µg/ml $Al(OH)_3$+25 µg/ml spike RBD protein solution. Stirred for 30 minutes in 4° C. environment, the mixture solution was treated with 9000 rpm for 5 min centrifugation. After centrifugation, took 160 µl supernatant solution and added 40 µl Bradford kit. Refer to FIG. 1. Prepared a spike RBD protein calibration curve from 50 µg/ml, 40 µg/ml. 25 µg/ml, 20 µg/ml, 12.5 µg/ml, 10 µg/ml, 6.25 µg/ml, 5 µg/ml and 2.5 µg/ml. The absorption rate is (1−concentration in the supernatant solution/25)×100.

Figure 2:
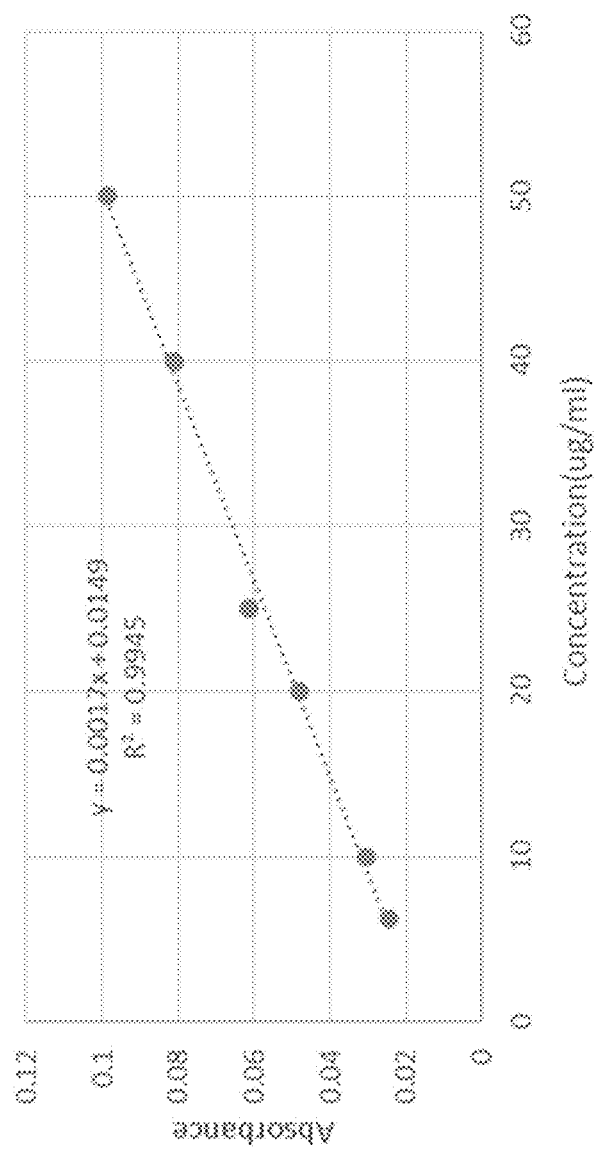
FIG. 2 is a calibration curve of spike RBD protein in AGO™ (amphiphilic polysaccharide) encapsulation according to an embodiment of the present invention.

AGO™ (Amphiphilic Polysaccharide) Encapsulation:

Took 0.5 ml $Al(OH)_3$ solution (1 mg/ml) and 0.5 ml spike RBD protein solution (50 µg/ml) to form a mixture of 500 µg/ml $Al(OH)_3$+25 µg/ml spike RBD protein solution. Stirred for 30 minutes in 4° C. environment, the mixture solution was then poured into an AGO™ (amphiphilic polysaccharide) aqueous solution with 3 mg of AGO™ (amphiphilic polysaccharide) powder. Stirred the other AGO™ (amphiphilic polysaccharide) aqueous solution with 3 mg of AGO™ (amphiphilic polysaccharide) powder for 24 hours in double distilled water in 4° C. environment. The $Al(OH)_3$+spike RBD protein+AGO™ (amphiphilic polysaccharide) solution and the other AGO™ (amphiphilic polysaccharide) solution were treated with 12000 rpm for 10 min centrifugation. After centrifugation, supernatant solution in which certain amount of free-form spike RBD protein remained was needed for further analysis. Refer to FIG. 2. Followed the same procedure to prepare a spike RBD protein calibration curve from 50 µg/ml, 40 µg/ml, 25 µg/ml, 20 µg/ml, 12.5 µg/ml, 10 µg/ml, 6.25 µg/ml, 5 µg/ml and 0 µg/ml. Bradford kit was used to measure the spike RBD protein concentration in the supernatant solution. Moreover, in order to effectively remove the noise of AGO™ (amphiphilic polysaccharide) under detection, pure AGO™ (amphiphilic polysaccharide) was used as reference solution, after then, a noise-free precise spike RBD protein measurement was obtained through the calculation of (1−concentration in the supernatant solution/25)×100 to obtain spike RBD protein encapsulation efficiency.

In this AGO™ (amphiphilic polysaccharide) encapsulation, it was found that the spike RBD protein encapsulation efficiency was as high as 90%, indicating that even if the spike RBD protein was not adsorbed with $Al(OH)_3$, the free-form spike RBD protein could be encapsulated by AGO™ (amphiphilic polysaccharide) with high efficiency.

Figure 3:
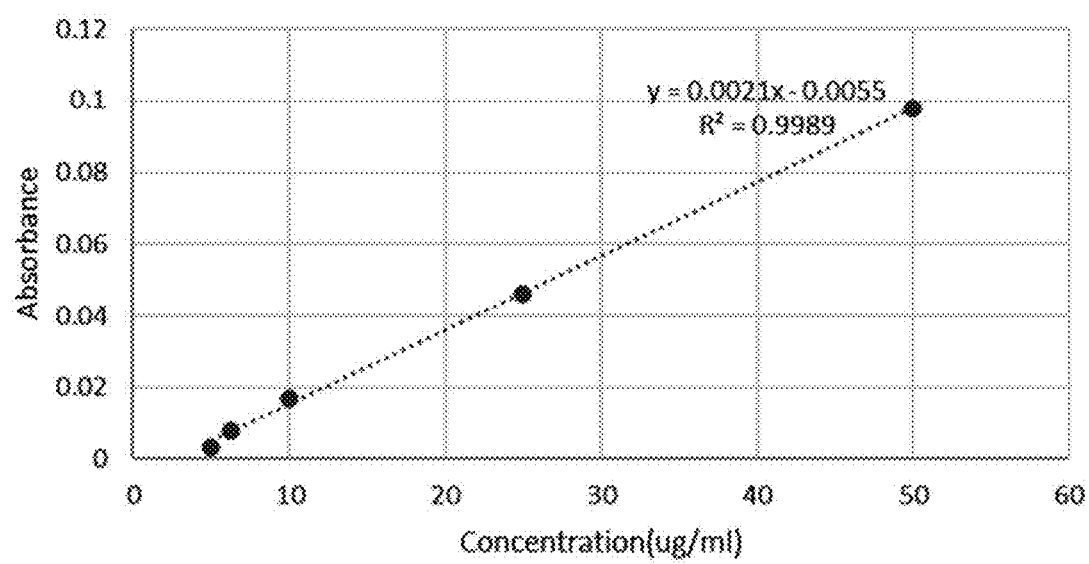
FIG. 3 is a calibration curve of spike RBD protein in Dual-adjuvant co-encapsulation according to an embodiment of the present invention.
Figure 4:
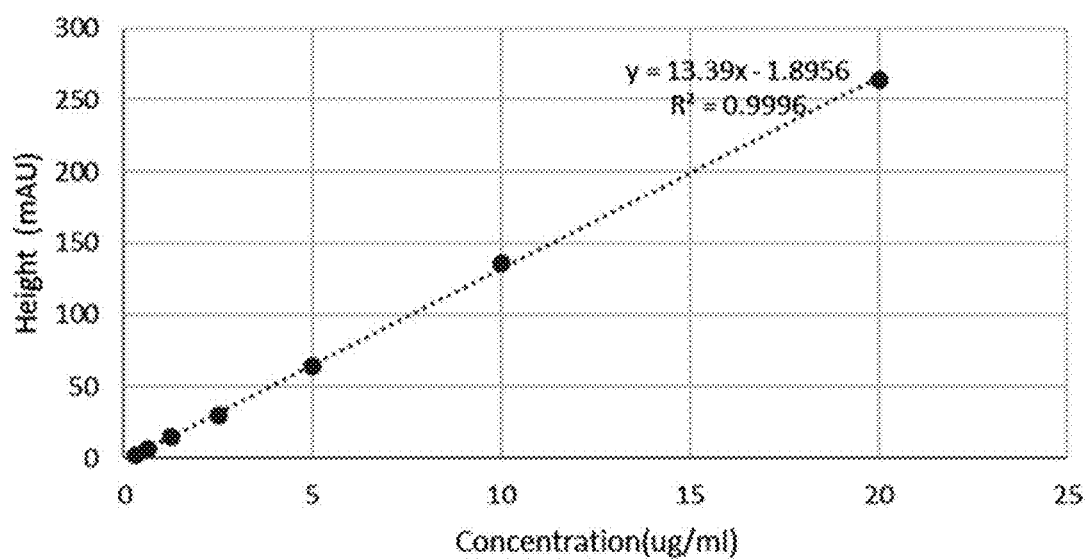
FIG. 4 is a calibration curve of CpG-ODN in Dual-adjuvant co-encapsulation according to an embodiment of the present invention.

Dual-Adjuvant ($Al(OH)_3$ and CpG-ODN) Co-Encapsulation:

Followed the same procedure disclosed in AGO™ (amphiphilic polysaccharide) encapsulation, where Encapsulation Efficiency (EE) of $Al(OH)_3$+spike RBD protein+CpG-ODN in 0.3 wt % AGO™ (amphiphilic polysaccharide) was also determined, and the calibration curves for both spike RBD protein and CpG-ODN were experimentally determined as FIG. 3 and FIG. 4. The calibration curves of both spike RBD protein and CpG-ODN were used to determine the amount of both adjuvants encapsulated into the AGO™ (amphiphilic polysaccharide). The EE of both spike RBD protein and CpG-ODN was measured respectively. Refer to the table below.

| $Al(OH)_3$:spike RBD protein:CpG-ODN (µg/ml) | EE of spike RBD protein | EE of CpG-ODN |
|---|---|---|
| 250:25:20 | 55% | 62% |
| 250:50:20 | 65% | 60% |

The present invention provides a composite-type nano-vaccine particle obtained by implementing the above three preparation procedures. The composite-type nano-vaccine particle comprises an active ingredient, spike RBD protein (SEQ ID NO:1), two adjuvants as aluminium salt ($Al(OH)_3$) nanoparticle adsorbed with the spike RBD protein and synthetic oligonucleotides (CpG-ODN, SEQ ID NO:2), and an amphiphilic alginate-based nanocarrier (AGO™ (amphiphilic polysaccharide)) encapsulating the active ingredient and the two adjuvants.

II. Measurement of Diameter and Zeta Potential of Composite-Type Nano-Vaccine Particle Dynamic light scattering (DLS) system is an easy and widely-used tool to measure particle size and zeta potential of a given particulate system. The DLS technique is an ideal method for measuring the particle size of suspensions from 1 nm to about 10 micrometers.

Adequate characterization of nanoparticles is of paramount importance to develop well defined nanoformulations of therapeutic relevance. Determination of particle size and surface charge of nanoparticles are indispensable for proper characterization of nanoparticles. DLS and zeta potential measurements have gained popularity as simple, easy and reproducible tools to ascertain particle size and surface charge, and can be adapted as a measure of quality control for the materials prepared.

Figure 5:
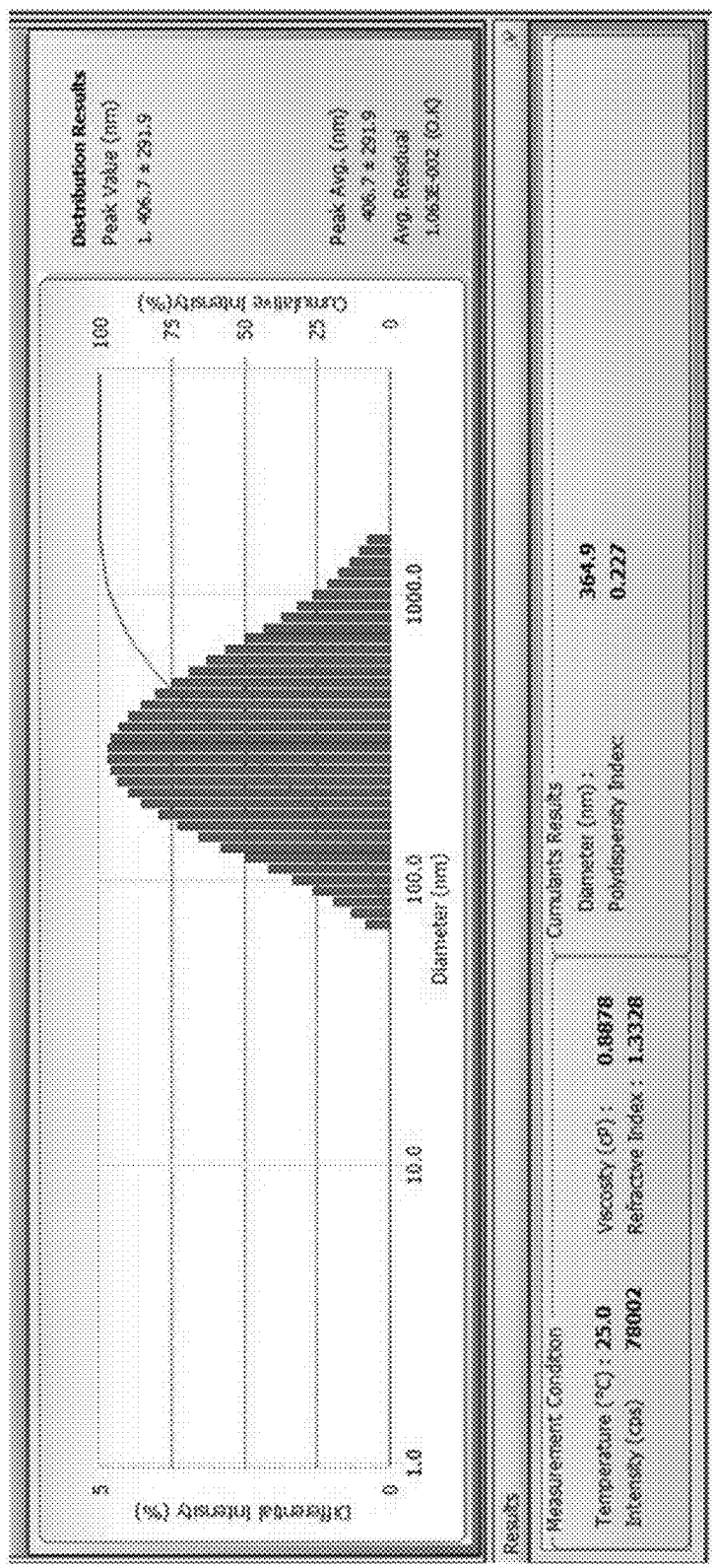
FIG. 5 is a diagram illustrating the DLS measurement of 0.1 wt % AGO™ (amphiphilic polysaccharide) with 0.00125 wt % spike RBD protein according to an embodiment of the present invention.

Refer to FIG. 5. Diameter and zeta potential of 0.1 wt % AGO™ (amphiphilic polysaccharide) with 0.00125 wt % spike RBD protein are 446.9±53.3 nm and −29.85±0.66 mV.

Figure 6:
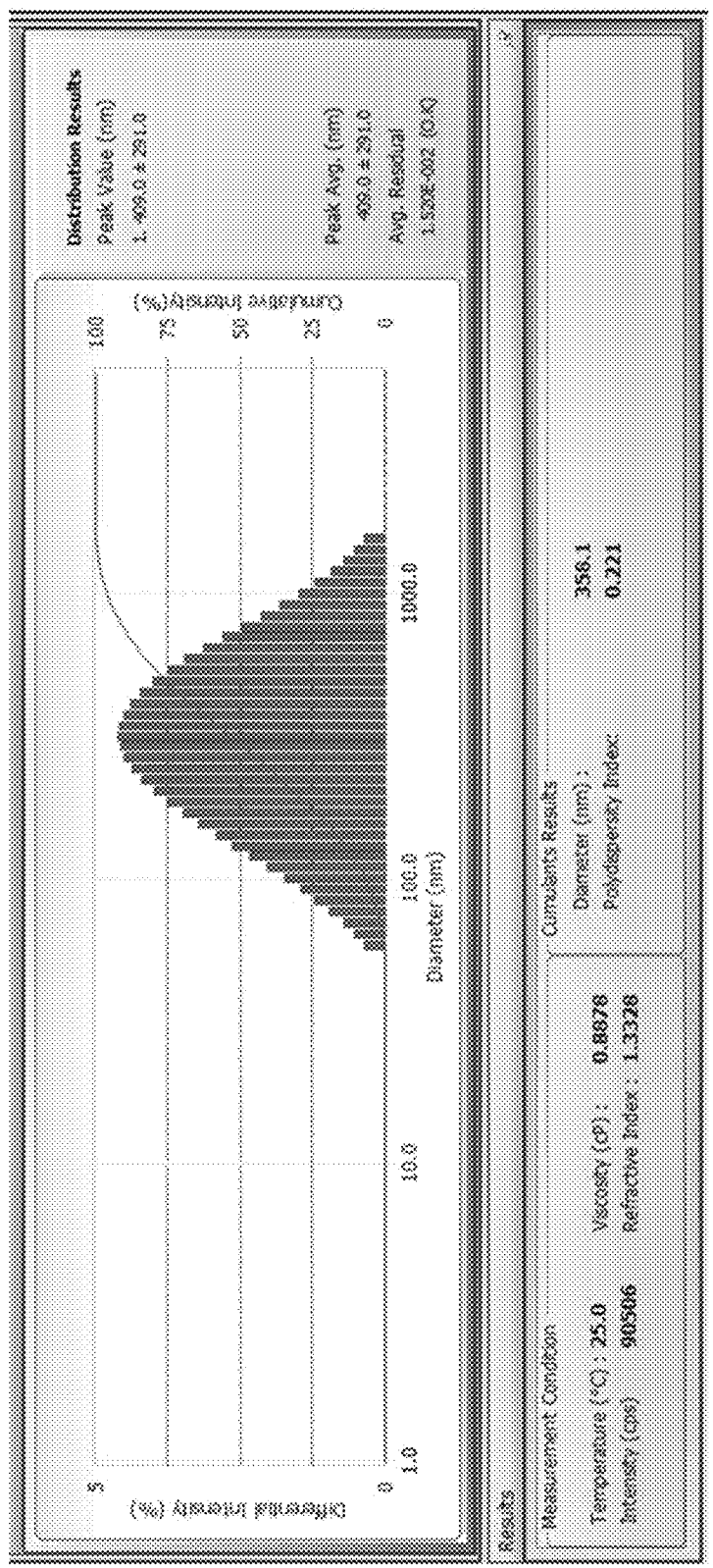
FIG. 6 is a diagram illustrating the DLS measurement of 0.1 wt % AGO™ (amphiphilic polysaccharide) with 0.0025 wt % spike RBD protein according to an embodiment of the present invention.

Refer to FIG. 6. Diameter and zeta potential of 0.1 wt % AGO™ (amphiphilic polysaccharide) with 0.0025 wt % spike RBD protein are 421.9±38.6 nm and −34.58±0.27 mV.

Figure 7:
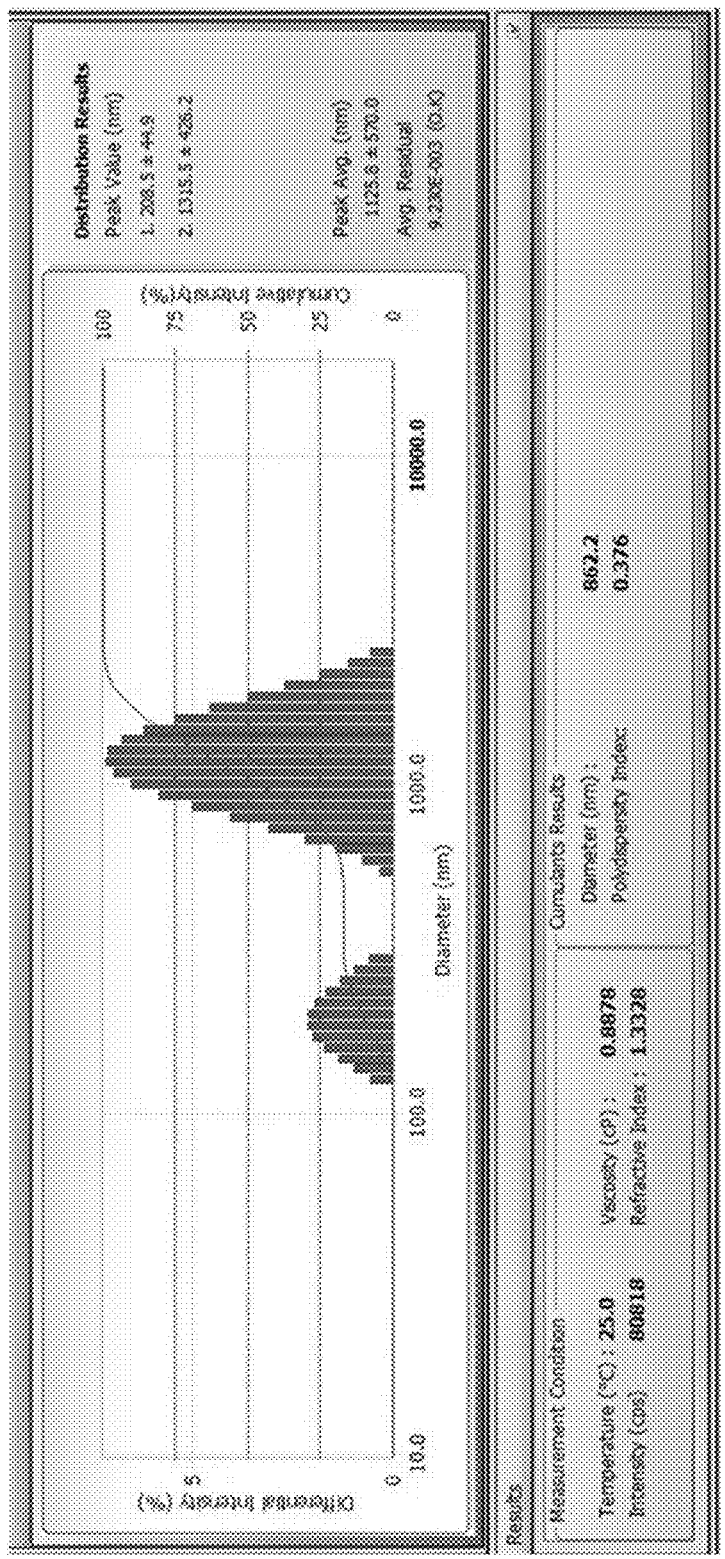
FIG. 7 is a diagram illustrating the DLS measurement of 0.1 wt % AGO™ (amphiphilic polysaccharide) with 0.025 wt % $Al(OH)_3$+0.00125 wt % spike RBD protein according to an embodiment of the present invention.

Refer to FIG. 7. Diameter and zeta potential of 0.1 wt % AGO™ (amphiphilic polysaccharide) with 0.025 wt % $Al(OH)_3$+0.00125 wt % spike RBD protein are 1168.4±94.2 nm and −29.13±1.67 mV. The ratio of spike RBD protein to $Al(OH)_3$ is 1:20.

Figure 8:
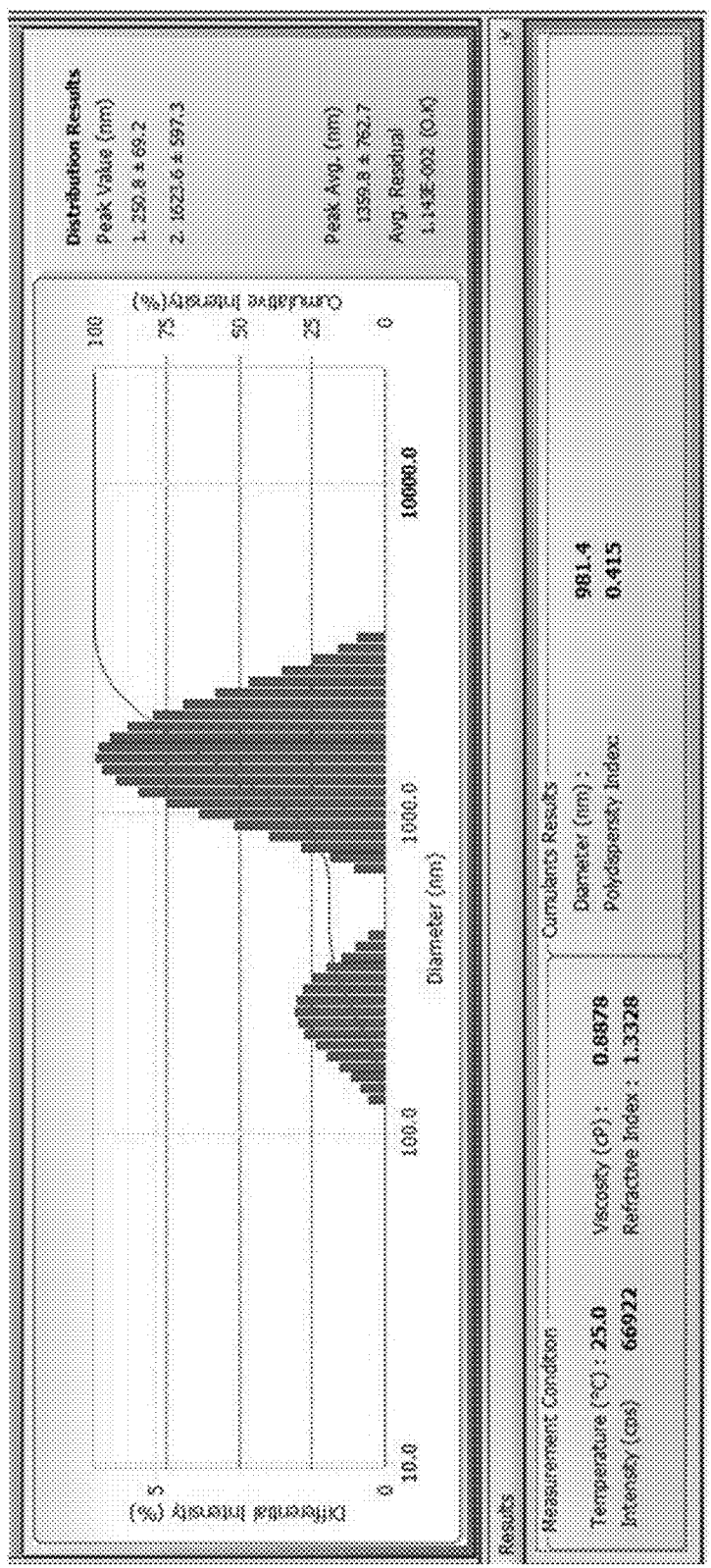
FIG. 8 is a diagram illustrating the DLS measurement of 0.1 wt % AGO™ (amphiphilic polysaccharide) with 0.025 wt % $Al(OH)_3$+0.0025 wt % spike RBD protein according to an embodiment of the present invention.

Refer to FIG. 8. Diameter and zeta potential of 0.1 wt % AGO™ (amphiphilic polysaccharide) with 0.025 wt % $Al(OH)_3$+0.0025 wt % spike RBD protein are 1349.4±41.5 nm and −33.87±0.22 mV. The ratio of spike RBD protein to $Al(OH)_3$ is 1:10.

Figure 9:
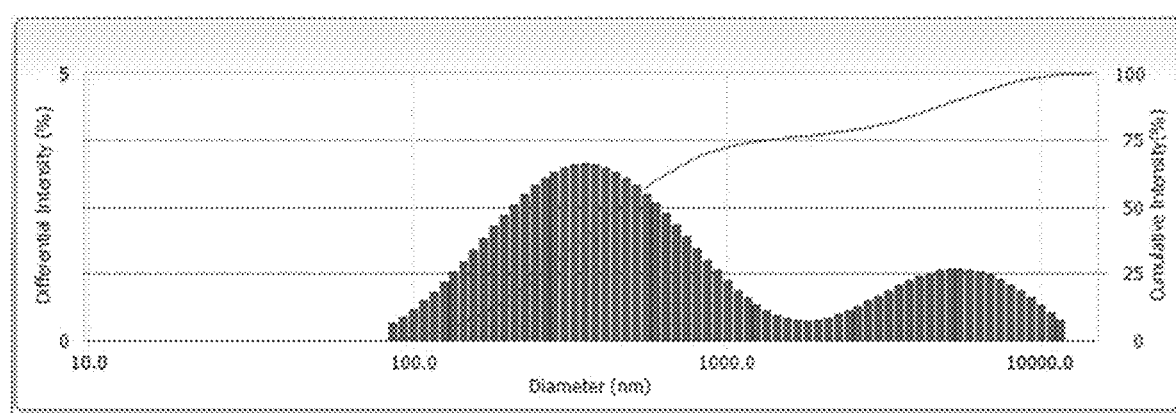
FIG. 9 is a diagram illustrating the DLS measurement of 0.3 wt % AGO™ (amphiphilic polysaccharide) with $Al(OH)_3$+spike RBD protein+CpG-ODN ($Al(OH)_3$:spike RBD protein:CpG-ODN 500:25:20 (μg/ml)) according to an embodiment of the present invention.

Refer to FIG. 9. Diameter and zeta potential of 0.3 wt % AGO™ (amphiphilic polysaccharide) with $Al(OH)_3$+spike RBD protein+CpG-ODN ($Al(OH)_3$:spike RBD protein:CpG-ODN 500:25:20 (µg/ml)) are 465.6±312.1 nm and −35.69±0.37 mV.

Figure 10:
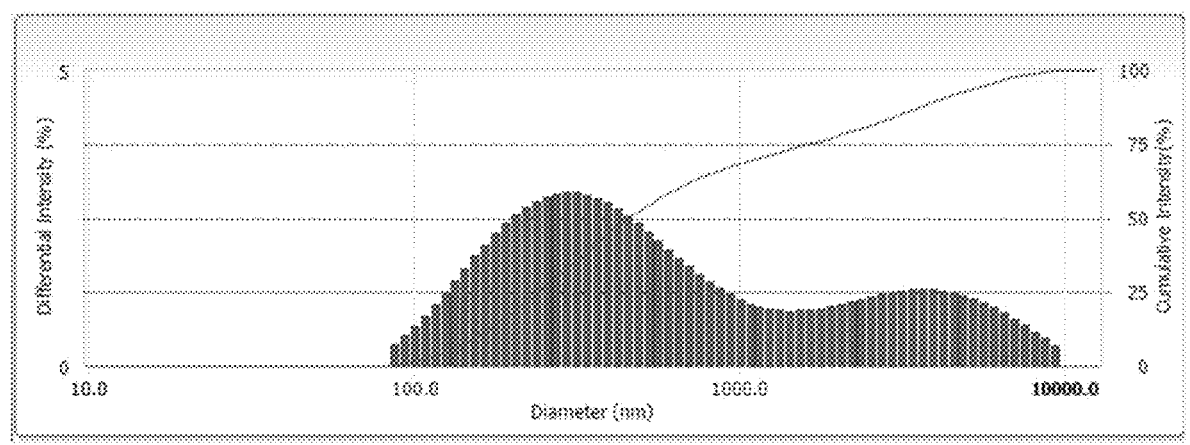
FIG. 10 is a diagram illustrating the DLS measurement of 0.3 wt % AGO™ (amphiphilic polysaccharide) with $Al(OH)_3$+spike RBD protein+CpG-ODN ($Al(OH)_3$:spike RBD protein:CpG-ODN 500:50:20 (μg/ml)) according to an embodiment of the present invention.

Refer to FIG. 10. Diameter and zeta potential of 0.3 wt % AGO™ (amphiphilic polysaccharide) with $Al(OH)_3$+spike RBD protein+CpG-ODN ($Al(OH)_3$:spike RBD protein:CpG-ODN 500:50:20 (µg/ml)) are 423.0±288.8 nm and −33.88±0.63 mV.

The surface charge of the composite-type nano-vaccine particle is proven negatively charged. The composite-type nano-vaccine particle has a particle size ranging from 300 nm to 1400 nm in diameter, which allows high amount of dual-adjuvant-antigen complex co-encapsulated and co-delivered into the targeting cells in host, permitting higher vaccine concentration to work out with desired immunological response, in a lower dosing amount.

III. Experiment of Cellular Endocytosis

Human colorectal adenocarcinoma cells (Caco2 cells) and African green monkey kidney epithelial cells (Vero E6 cells) in which both cells present ACE2 cellular receptors on cell membrane were used to conduct cellular endocytosis experiments. The composite-type nano-vaccine particles were designed into two types, AGO™ (amphiphilic polysaccharide) nanoparticles with spike RBD protein and AGO™ (amphiphilic polysaccharide) nanoparticles without spike RBD protein. Spike RBD protein is originally designed as targeting moiety toward ACE2 cellular receptor on cell membrane. Caco2 cells and Vero E6 cells were treated respectively with the two types of AGO™ (amphiphilic polysaccharide) nanoparticles and observed for 8 hours. The two types of AGO™ (amphiphilic polysaccharide) nanoparticles were stained yellow-green dots in FIGS. 11A, 11B, 13A and 13B.

Figure 11A:
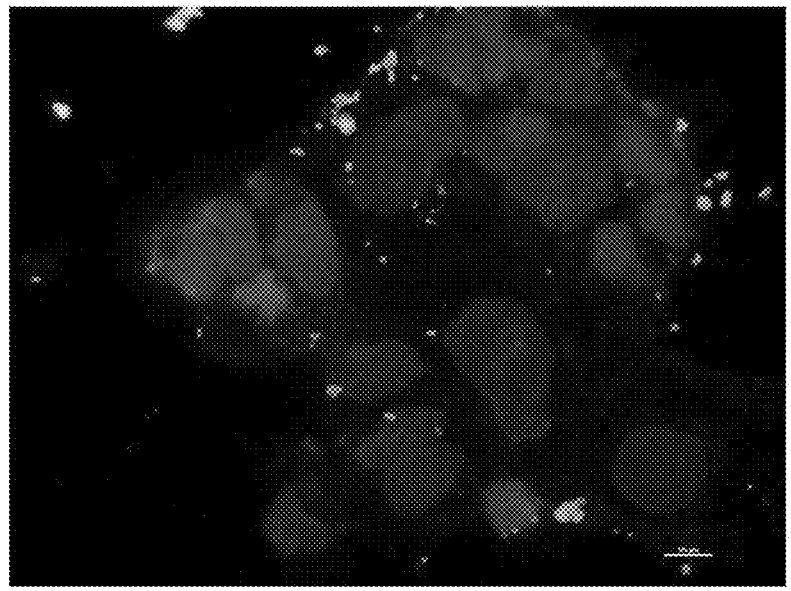
FIG. 11A is an immunofluorescent staining images showing Caco2 cells endocytosed AGO™ (amphiphilic polysaccharide) nanoparticles without spike RBD protein according to an embodiment of the present invention.
Figure 11B:
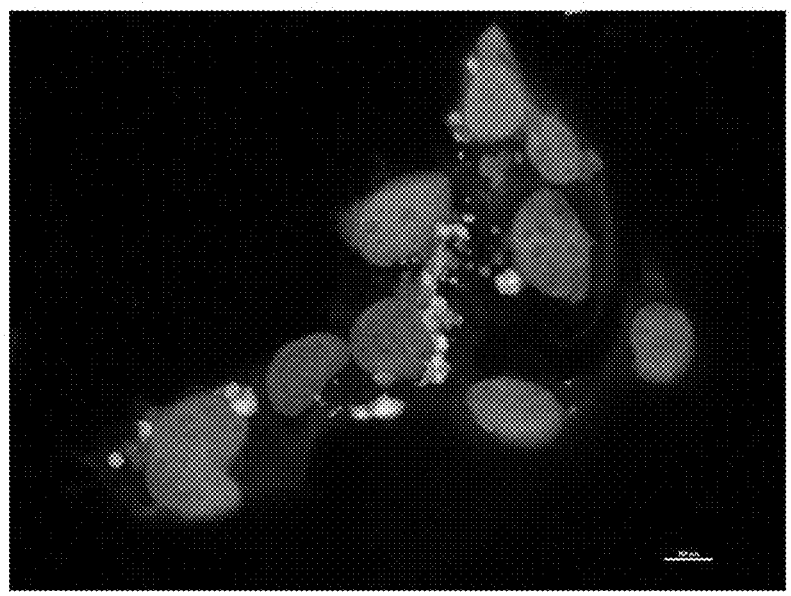
FIG. 11B is an immunofluorescent staining images showing Caco2 cells endocytosed AGO™ (amphiphilic polysaccharide) nanoparticles with spike RBD protein according to an embodiment of the present invention.
Figure 12:
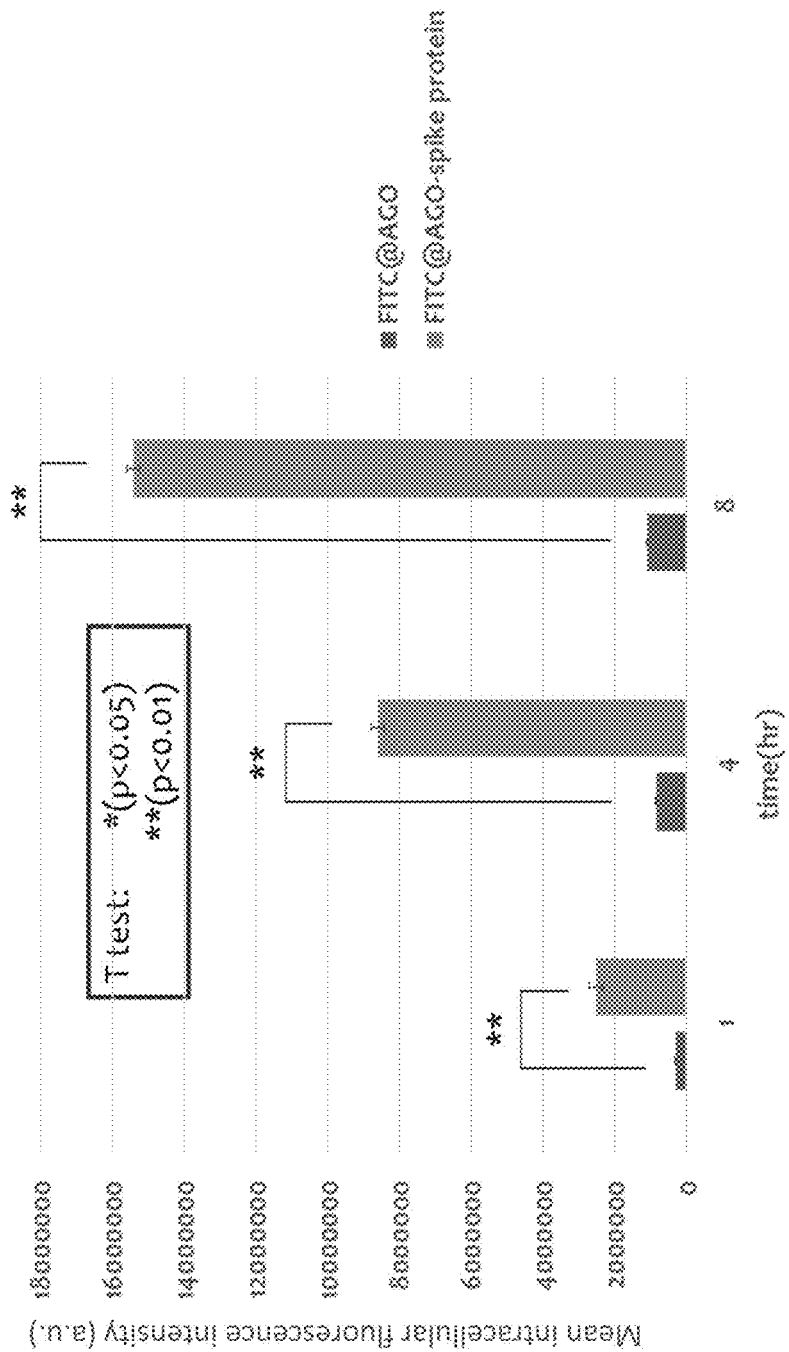
FIG. 12 is a bar chart illustrating the statistical difference between two types of AGO™ (amphiphilic polysaccharide) nanoparticles in cellular endocytosis experiment according to an embodiment of the present invention.
Figure 13A:
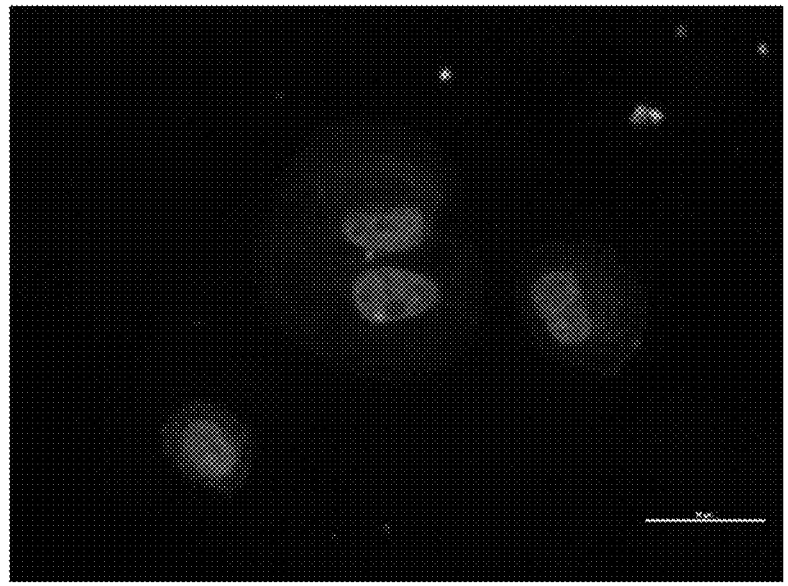
FIG. 13A is an immunofluorescent staining images showing Vero E6 cells endocytosed AGO™ (amphiphilic polysaccharide) nanoparticles without spike RBD protein according to an embodiment of the present invention.
Figure 13B:
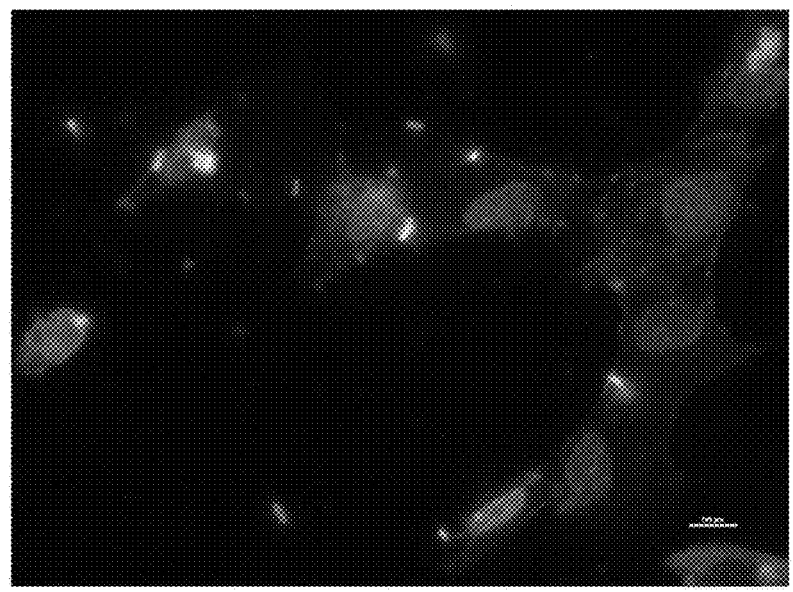
FIG. 13B is an immunofluorescent staining images showing Vero E6 cells endocytosed AGO™ (amphiphilic polysaccharide) nanoparticles with spike RBD protein according to an embodiment of the present invention.

Refer to FIGS. 11A and 11B. The two types of AGO™ (amphiphilic polysaccharide) nanoparticles were endocytosed largely and efficiently by the Caco2 cells and the difference in the amount endocytosed is hard to quantitatively differentiate between the nanoparticles with or without spike RBD protein conjugation. One finding in FIGS. 11A and 11B is that the AGO™ (amphiphilic polysaccharide) nanoparticles without spike RBD protein appeared to be residing mostly in the region of cytoplasm (stained red), while the AGO™ (amphiphilic polysaccharide) nanoparticle with spike RBD protein is largely surrounding the cell nuclei (stained blue). This finding suggests the AGO™ (amphiphilic polysaccharide) nanoparticles with spike RBD protein allowed to be more potentially triggered a desired biological response such as immunological potency. Refer to FIG. 12. However, statistically, there were obvious differences between the two types of AGO™ (amphiphilic polysaccharide) nanoparticles in this cellular endocytosis experiment. Refer to FIGS. 13A and 13B. AGO™ (amphiphilic polysaccharide) nanoparticles were endocytosed by the Vero E6 cells and appeared to have more AGO™ (amphiphilic polysaccharide) nanoparticles internalized in the cytoplasm regions (stained red) and regions near cell nuclei (stained blue) with spike RBD protein conjugation.

The spike RBD protein conjugated in the AGO™ (amphiphilic polysaccharide) serves as dual-function moiety to the composite-type nano-vaccine particle. The spike RBD protein and ACE2 cellular receptor binding is not only through the mechanism of electrostatic interaction on account that the spike RBD protein shows positively surface charged and ACE2 shows negatively charged under physiological condition, but a strong donor-receptor binding.

IV. In Vitro Cytotoxicity Test

L929 mouse fibroblast cells (L929 cells) were used to conduct an in vitro cytotoxicity test. L929 cells were treated with the AGO™ (amphiphilic polysaccharide) nanoparticles with spike RBD protein in different concentration for 24 hours culture.

Figure 14:
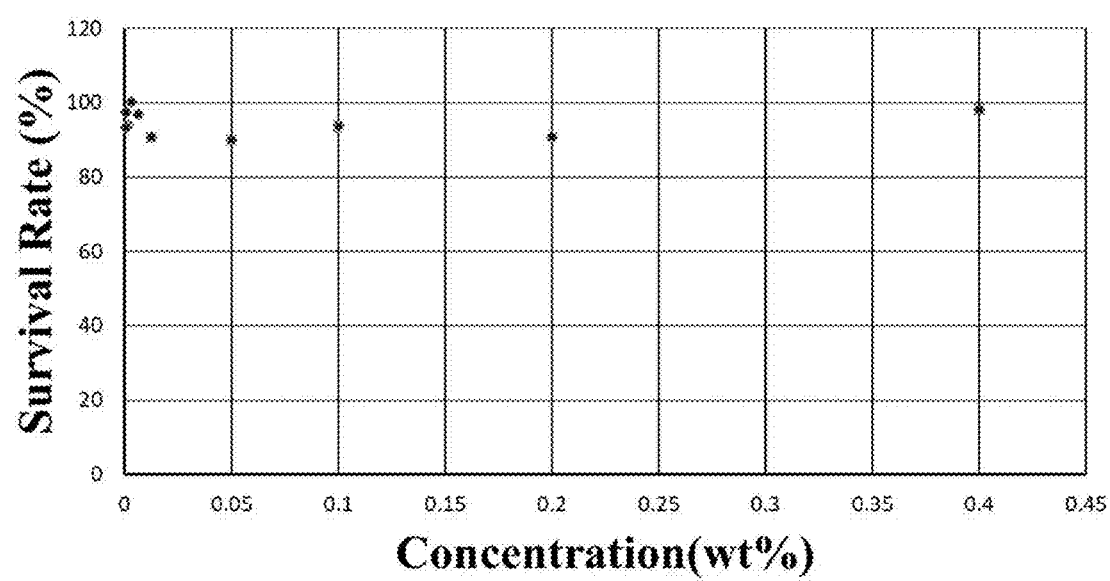
FIG. 14 is a diagram illustrating in vitro cytotoxicity of AGO™ (amphiphilic polysaccharide) nanoparticles with spike RBD protein against L929 cells according to an embodiment of the present invention.

Refer to FIG. 14. The results of survival rate of L929 cells treated with the AGO™ (amphiphilic polysaccharide) nanoparticles with spike RBD protein in different concentration presented over 80% in consistency. The cell culture in vitro cytotoxicity test indicated the AGO™ (amphiphilic polysaccharide) nanoparticles with spike RBD protein showed excellent cyto-compatibility even at a higher concentration against L929 cells.

V. Cell Viability Test

Vero E6 cells were used to conduct cell viability test. Vero E6 cells were cultured with dual-adjuvant ($Al(OH)_3$ and CpG-ODN) nano-vaccine particle with a concentration ranging from 0.01 wt % to 0.6 wt % for 24 hours. The dual-adjuvant ($Al(OH)_3$ and CpG-ODN) nano-vaccine particle was made from $Al(OH)_3$:spike RBD protein:CpG-ODN 500:50:20 (μg/ml) encapsulated into the AGO™ (amphiphilic polysaccharide).

Figure 15:
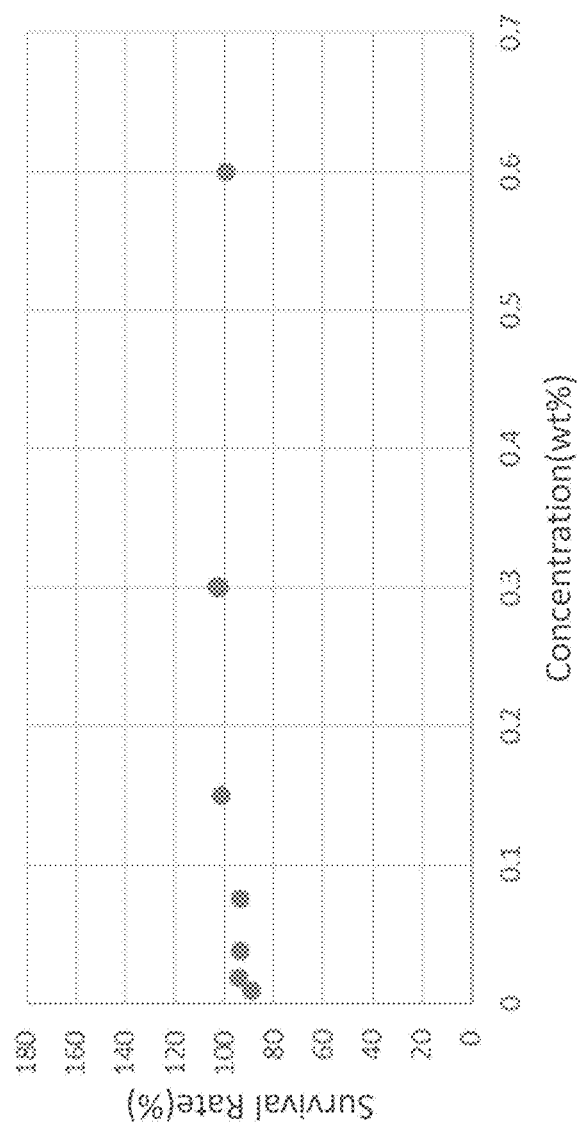
FIG. 15 is a diagram illustrating cell viability of Vero E6 cells cultured with dual-adjuvant nano-vaccine particle with different concentration according to an embodiment of the present invention.

Refer to FIG. 15. Result of the cell viability test of Vero E6 cells showed excellent cyto-compatibility against the dual-adjuvant ($Al(OH)_3$ and CpG-ODN) nano-vaccine particle, indicating the present invention is highly biocompatible.

The foregoing embodiments are illustrative of the characteristics of the present invention so as to enable a person skilled in the art to understand the disclosed subject matter and implement the present invention accordingly. The embodiments, however, are not intended to restrict the scope of the present invention. Hence, all equivalent modifications and variations made in the foregoing embodiments without departing from the spirit and principle of the present invention should fall within the scope of the appended claims.

What is claimed is:

1. A nano-vaccine particle, comprising:
an amphiphilic carrier;
an active ingredient; and
at least one adjuvant,
wherein the nano-vaccine particle shows a negatively-charged surface, and
wherein the amphiphilic carrier encapsulates the active ingredient and the adjuvant,
wherein the active ingredient is a spike receptor-binding domain protein of SARS-CoV-2, and
wherein an amino acid sequence of the spike receptor-binding domain protein is set forth by SEQ ID NO:1.

2. The nano-vaccine particle of claim 1, wherein the nano-vaccine particle has a particle size ranging from 300 nm to 1400 nm in diameter.

3. The nano-vaccine particle of claim 1, wherein the active ingredient is conjugate to the amphiphilic carrier.

4. The nano-vaccine particle of claim 1, wherein the amphiphilic carrier is a carrier comprising alginate polysaccharides.

5. The nano-vaccine particle of claim 4, wherein the amphiphilic carrier comprising alginate polysaccharides has a self-assembly behavior in aqueous solution to form a nanoparticle.

6. The nano-vaccine particle of claim 1, wherein the spike RBD protein changes in charging in accordance with pH adjustment in a solution.

7. The nano-vaccine particle of claim 1, wherein the at least one adjuvant comprises aluminium salt, synthetic oligonucleotides, or a combination thereof.

8. The nano-vaccine particle of claim 7, wherein a nucleotide sequence of the synthetic oligonucleotides is set forth by SEQ ID NO:2.

9. The nano-vaccine particle of claim 1, wherein the active ingredient is adsorbed with the adjuvant.

10. The nano-vaccine particle of claim 1, wherein a biocompatible dose of the nano-vaccine particle is in a concentration between 0.01 wt % to 0.6 wt %.

* * * * *